(12) United States Patent
Lewallen (10) Patent No.: US 6,749,639 B2
(45) Date of Patent: Jun. 15, 2004

(54) COATED PROSTHETIC IMPLANT (75) Inventor: David G. Lewallen, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 10/225,624

(22) Filed: Aug. 22, 2002

(65) Prior Publication Data

US 2003/0045941 A1 Mar. 6, 2003

Related U.S. Application Data (60) Provisional application No. 60/315,128, filed on Aug. 27, 2001.

(51) Int. Cl.$^7$ ................. A61F 2/28; A61F 2/36
(52) U.S. Cl. ................. 623/23.57; 623/23.26; 623/23.36
(58) Field of Search .............. 623/23.15, 23.23, 623/23.25, 23.26, 23.36, 23.37, 23.46, 23.57, 23.58

(56) References Cited

U.S. PATENT DOCUMENTS

| | | |
|---|---|---|
| 4,202,055 A * | 5/1980 | Reiner et al. ............ 623/23.57 |
| 4,338,926 A | 7/1982 | Kummer et al. |
| 4,404,691 A | 9/1983 | Buning et al. |
| 4,655,777 A | 4/1987 | Dunn et al. |
| 5,258,034 A | 11/1993 | Furlong et al. |
| 5,458,653 A | 10/1995 | Davidson |
| 5,480,438 A | 1/1996 | Arima et al. |
| 5,489,306 A * | 2/1996 | Gorski ..................... 623/23.55 |
| 5,507,833 A | 4/1996 | Bohn |
| 5,858,020 A | 1/1999 | Johnson et al. |
| 5,910,172 A | 6/1999 | Peneberg |
| 5,935,172 A | 8/1999 | Ochoa et al. |
| 6,013,104 A | 1/2000 | Kampner |
| 6,077,989 A | 6/2000 | Kandel et al. |
| 6,142,998 A | 11/2000 | Smith et al. |

* cited by examiner

Primary Examiner—Bruce Snow
(74) Attorney, Agent, or Firm—Quarles & Brady LLP (57) ABSTRACT

A prosthesis for implanting into a bone having a cavity is disclosed. The prosthesis comprises a body and a stem. A first coating including a bone ingrowth promoting material that promotes ingrowth of bone onto the stem and a bioabsorbable material that delays the ingrowth of bone onto the stem is disposed on a proximal portion of the stem outer surface. A second coating including the bone ingrowth promoting material and the bioabsorbable material is disposed on a distal portion of the stem outer surface. The ratio of bone ingrowth promoting material to bioabsorbable material in the first coating is greater than the ratio of bone ingrowth promoting material to bioabsorbable material in the second coating whereby the affixation of the bone to the proximal zone of the stem is faster and stronger over time than the affixation of the bone to the distal zone of the stem.

20 Claims, 2 Drawing Sheets

COATED PROSTHETIC IMPLANT

CROSS-REFERENCE TO RELATED APPLICATIONS

This application claims the benefit of U.S. Provisional Patent Application No. 60/315,128 filed Aug. 27, 2001.

STATEMENT REGARDING FEDERALLY SPONSORED RESEARCH

Not Applicable.

BACKGROUND OF THE INVENTION

1. Field of the Invention

This invention relates to implantable bone prostheses, and more particularly to joint prostheses that attach to bone and have variable bone affixation rates and final strengths at different locations on the prosthesis.

2. Description of the Related Art

The replacement of joints, such as the shoulder, hip, knee, ankle and wrist, with prosthetic implants has become widespread. The size, shape and materials of a joint prosthesis affect the extent of bone growth into and surrounding the prosthesis, both of which contribute to fixation of the prosthesis within the patient's bone.

Joint prostheses may be affixed to or within natural bone using bone cements. While bone cements provide the initial fixation necessary for healing following surgery, bone cements often result in a very stiff overall structure, are prone to loosening with time, and can provoke tissue reactions.

Because of the disadvantages associated with the use of bone cements, "cementless" or "press fit" implants have been developed. Various procedures are used to affix a cementless or press fit implant to bone. In one procedure, the surface of the implant is coated with a porous material which allows the patient's bone to grow into the pores, thereby mechanically fixing the implant to bone. In another procedure, the surface of the implant is coated with a material, such as hydroxyapatite, which can chemically bond the implant to bone. As a result of either procedure, the implant is biologically attached to the bone in that the patient's own tissue eventually holds the implant securely in place, either mechanically or chemically, and the implant subsequently becomes a permanent part of the bone.

Typically, a cementless or press-fit implant requires immediate rigid fixation to the bone for a sufficient time period (e.g., at least six to twelve weeks) to assure mechanical attachment or chemical bonding to the bone. If the implant is not held rigidly, micro-motion occurs at the implant-bone interface. The result is a less stable fibrous tissue interface rather than the necessary, more stable, securely-fixed bony attachment. One method for holding the implant rigidly in the bone involves the use of an implant with a stem. The stem "press-fits" into the intramedullary canal of the bone (e.g., the femur) to hold the implant rigidly in the bone and thereby allows for an adequate mechanical attachment or chemical bonding for secure fixation.

A recognized problem with the use of an interference fit (press-fit) stem is that transfer of stress from the implant to the bone is abnormal. Instead of a normal loading of the bone primarily at the end of the bone near the joint surface, the bone is loaded more distally where the stem of the implant contacts and/or is affixed to the bone. This results in a phenomenon called "stress shielding" in which the load (i.e., stress) bypasses or "unloads" the end of the joint surface portion of the bone. As a result, the joint surface portion of the bone undergoes resorption, (i.e., the bone retreats from its tight fit around the prosthetic implant) thereby introducing some "play" into the fit. This leads to weakening over a period of years, thus creating a potential for fracture or a loosening of the implant within the bone.

Various methods have been proposed to solve the aforementioned stress shielding problems. For example, U.S. Pat. No. 5,458,653 discloses a hip joint stem that has a biocompatible bioabsorbable polymer coating on selected locations of the stem. The polymer coating initially retards anchoring of the stem to the bone at the selected locations. When the polymer coating is absorbed into the body, bone ingrowth can occur in the spaces left behind by the polymer. In one version of this hip joint stem, the thickest part of the polymer coating is located at the distal end of the stem and the thinnest part of the polymer coating is located at the proximal end of the stem. In this arrangement of the polymer coating, the coating is absorbed progressively and gradually from the stem such that bone affixation progresses down the length of the stem to the distal end of the stem. U.S. Pat. Nos. 6,013,104, 5,935,172, 5,528,034, and 5,507,833 also disclose similar techniques in which a prosthesis includes bioabsorbable coatings or sleeves to control bone ingrowth.

Upon review of the foregoing methods that have been proposed to solve the problems associated with stress shielding in a prosthetic implant, it appears that U.S. Pat. No. 5,458,653 may describe the most sophisticated solution. Specifically, the method in U.S. Pat. No. 5,458,653 in which the thickness of the bioabsorbable polymer coating is varied along the length of the stem can provide for bone affixation that progresses down the length of the stem to the base distal end of the stem. Although this method could be a valuable tool for eliminating stress shielding in a prosthetic implant, it does have one significant disadvantage. While a manufacturer of this coated implant can provide an implant having a stem with a bioabsorbable polymer coating of varying thickness, it would be very difficult for a surgeon to precisely alter the thickness of the polymer coating on the coated implant or to apply a bioabsorbable polymer coating of varied thickness to the stem of an uncoated implant during surgery. Therefore, the orthopedic surgeon is essentially limited to an implant with a stem having a bioabsorbable polymer coating of predetermined thicknesses set by the manufacturer. This limits the surgeon's ability to control bone affixation at different locations on the prosthesis.

Therefore, there is a need for an implantable bone prosthesis and associated surgical methods that provide an improved solution to the problems associated with stress shielding and that allow a surgeon to control bone affixation rates and final strengths at different locations on a prosthesis.

SUMMARY OF THE INVENTION

The foregoing needs are met by a prosthesis for implanting into a bone in accordance with the invention. The prosthesis comprises a body and a stem that extends away from the body. The stem has an outer surface and is dimensioned to be inserted into a cavity of the bone. A first coating including a bone ingrowth promoting material that promotes ingrowth of bone onto the stem and a bioabsorbable material that delays the ingrowth of bone onto the stem is disposed on a proximal portion of the outer surface of the stem. A second coating including the bone ingrowth promoting material and the bioabsorbable material is disposed on a distal portion of the outer surface of the stem. The ratio of the bone ingrowth promoting material to the bioabsorbable material in the first coating is greater than the ratio of the bone ingrowth promoting material to the bioabsorbable material in the second coating. By formulating the first coating with a higher ratio of the bone ingrowth promoting material to the bioabsorbable material, it is possible to implant the prosthetic implant in the bone such that the affixation of the bone to the proximal zone of the stem is faster and stronger over time than the affixation of the bone to the distal zone of the stem.

In another aspect of the invention, the first coating and the second coating may include different bone ingrowth promoting materials and different bioabsorbable materials. The bone ingrowth promoting materials and the bioabsorbable materials are selected such that the first coating promotes faster and greater bone ingrowth onto the stem compared to the second coating. As a result, it is also possible to implant the prosthetic implant in the bone such that the affixation of the bone to the proximal zone of the stem is faster and stronger over time than the affixation of the bone to the distal zone of the stem.

In yet another aspect of the invention, there is provided a method for implanting a prosthesis in a bone. The method involves applying a first coating including a bone ingrowth promoting material and a bioabsorbable material onto a proximal portion of a stem of a prosthesis and applying a second coating including the bone ingrowth promoting material and the bioabsorbable material to a distal portion of the stem of the prosthesis. The prosthesis is then inserted into a cavity in a bone such that the first coating and the second coating are placed in contact with the bone. By formulating the first coating and the second coating such that the ratio of the bone ingrowth promoting material to the bioabsorbable material in the first coating is greater than the ratio of the bone ingrowth promoting material to the bioabsorbable material in the second coating, it is possible to affix the prosthesis to the bone whereby the affixation of the bone to the proximal portion of the stem of the prosthesis is faster and stronger over time than the affixation of the bone to the distal portion of the prosthesis.

In still another aspect of the invention, there is provided another method for implanting a prosthesis in a bone. The method involves applying a first coating including a first bone ingrowth promoting material and a first bioabsorbable material onto the proximal portion of a stem of a prosthesis and applying a second coating including a second bone ingrowth promoting material and a second bioabsorbable material onto the distal portion of the stem of the prosthesis. The prosthesis is then located in a cavity of the bone such that the first coating and the second coating are placed in contact with the bone. By selecting the first and second bone ingrowth promoting material and the first and second bioabsorbable material such that the first coating promotes faster and greater bone ingrowth onto the prosthesis compared to the second coating, it is also possible to affix the prosthesis to the bone whereby the affixation of the bone to the proximal portion of the stem of the prosthesis is faster and stronger over time than the affixation of the bone to the distal portion of the stem of the prosthesis.

In a further aspect of the invention, there is provided a method for affixing a prosthesis to a bone. The method involves applying a first coating including a bone ingrowth promoting material and a bioabsorbable material onto a first portion of a prosthesis and applying a second coating including the bone ingrowth promoting material and the bioabsorbable material to a second portion of the prosthesis. The prosthesis is then located such that the first coating and the second coating are placed in contact with the bone. By formulating the first coating and the second coating such that the ratio of the bone ingrowth promoting material to the bioabsorbable material in the first coating is greater than the ratio of the bone ingrowth promoting material to the bioabsorbable material in the second coating, it is possible to affix the prosthesis to the bone whereby the affixation of the bone to the first portion of the prosthesis is faster and stronger over time than the affixation of the bone to the second portion of the prosthesis.

In still another aspect of the invention, there is provided another method for affixing a prosthesis to a bone. The method involves applying a first coating including a first bone ingrowth promoting material and a first bioabsorbable material onto a first portion of a prosthesis and applying a second coating including a second bone ingrowth promoting material and a second bioabsorbable material onto a second portion of the prosthesis. The prosthesis is then located such that the first coating and the second coating are placed in contact with the bone. By selecting the first and second bone ingrowth promoting material and the first and second bioabsorbable material such that the first coating promotes faster and greater bone ingrowth onto the prosthesis compared to the second coating, it is possible to affix the prosthesis to the bone whereby the affixation of the bone to the first portion of the prosthesis is faster and stronger over time than the affixation of the bone to the second portion of the prosthesis.

It is therefore an advantage of the present invention to provide a joint prosthesis that attaches to bone and has variable bone affixation rates at different locations on the prosthesis.

It is another advantage of the present invention to provide a joint prosthesis that attaches to bone and has variable final strengths over time at different locations on the prosthesis.

It is a further advantage of the present invention to provide a method for affixing a prosthesis to a bone wherein the prosthesis attaches to the bone with variable bone affixation rates at different locations on the prosthesis.

It is yet another advantage of the present invention to provide a method for affixing a prosthesis to a bone wherein the prosthesis attaches to the bone with variable final strengths over time at different locations on the prosthesis.

These and other features, aspects, and advantages of the present invention will become better understood upon consideration of the following detailed description, drawings, and appended claims.

It should be understood that the drawings are not necessarily to scale and that the embodiments are sometimes illustrated by diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

Like reference numerals will be used to refer to like or similar parts from Figure to Figure in the following description of the drawings.

DETAILED DESCRIPTION OF THE INVENTION

The present invention is directed to coated prostheses, methods for affixing a prosthesis to a bone, and methods for implanting a prosthesis in a bone. The methods and prosthesis illustrated and described herein are for the implantation of the femoral prosthesis component of an artificial hip joint in the femoral medullary canal. However, it should be understood that the methods and prostheses according to the invention can be used in the repair of any bone or in connection with the implantation of prosthetic devices at or in any bone in the body, adjacent to or remote from any joint, including without limitation the hip, knee and spinal joints. Further, the methods and prostheses according to the invention can be used in primary surgery, in which a prosthesis is being used to reconstruct a joint for the first time, as well as in revision surgery, in which a previously-implanted prosthesis is being replaced with another prosthesis. Press fit, cement or other fixation techniques can be employed in conjunction with the methods and prostheses according to the invention.

Figures 1, 2, 3:
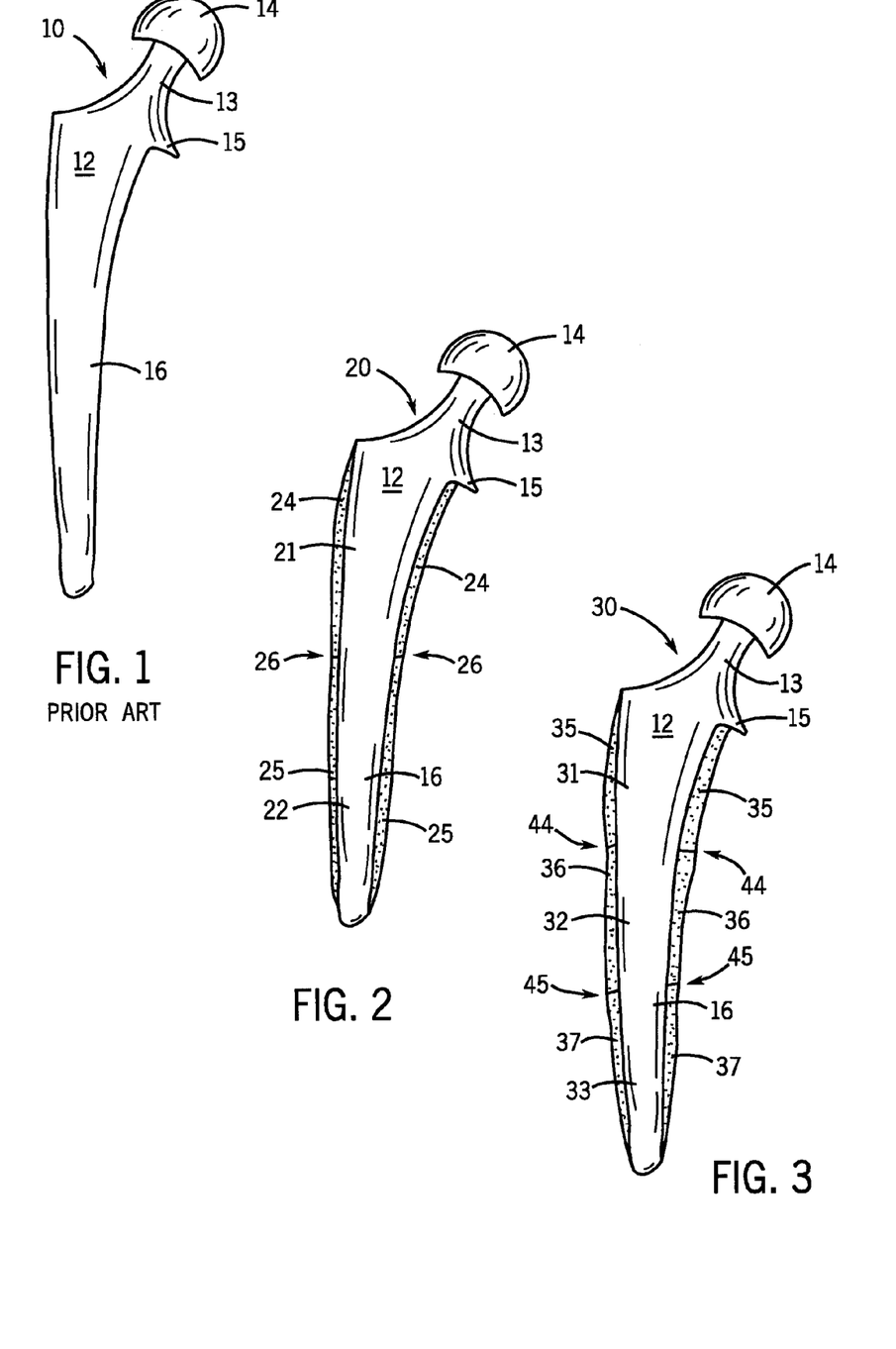
FIG. 1 is a side view of a prior art femoral prosthesis.
FIG. 2 is a side view of a femoral prosthesis according to the invention.
FIG. 3 is a side view of another femoral prosthesis according to the invention.

Referring first to FIG. 1, there is shown a prior art femoral prosthesis 10 that may be implanted in a resected femur as part of a hip replacement procedure. The prosthesis 10 includes a body 12 having a neck portion 13, a femoral head 14 and a collar 15. The femoral head 14 is received in an acetabular component (not shown) that is mounted in a patient's pelvis as is well known in the art. Extending away from the body 12 of the prosthesis 10 is a generally cylindrical or tubular stem 16 that is inserted within the intramedullary canal of the femur. The femoral prosthesis 10 may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone).

Referring now to FIG. 2, there is shown a coated femoral prosthesis 20 in accordance with one aspect of the present invention. The coated femoral prosthesis 20 includes a body 12 having a neck portion 13, a femoral head 14 and a collar 15, and a stem 16 as in the femoral prosthesis 10 of FIG. 1. The body and stem may be formed from the same materials as the femoral prosthesis 10 of FIG. 1. The stem 16 includes a proximal (or upper) portion 21 and a distal (or lower) portion 22. The outer surface of the proximal portion 21 of the stem 16 is coated with a first coating 24 (shown in cross-section) that includes (i) a bone ingrowth promoting material that promotes ingrowth of bone onto the stem when the femoral prosthesis 20 is located in the intramedullary canal of a femur, and (ii) a bioabsorbable material that delays the ingrowth of bone onto the stem. The outer surface of the distal portion 22 of the stem 16 is coated with a second coating 25 (shown in cross-section) that includes a bone ingrowth promoting material and a bioabsorbable material. The first coating 24 and the second coating 25 are arranged on the stem 16 of the prosthesis 20 such that the first coating 24 and the second coating 25 are in abutting relationship at an interface indicated at 26. The first coating 24 and the second coating 25 may be applied to the outer surface of the stem 16 either by the prosthesis manufacturer or by the surgeon at the time of the operation.

Having described the arrangement of the first coating 24 and the second coating 25 on the stem 16 of the prosthesis 20, the bone ingrowth promoting material and the bioabsorbable material that comprise the first coating 24 and the second coating 25 can be described in further detail. As used herein to describe a material, the term "bone ingrowth promoting" is used to define a material that will increase the speed at which an implant is chemically or mechanically affixed to bone by way of bone ingrowth compared to the speed at which an implant is affixed to bone without use of the material. Non-limiting examples of suitable bone ingrowth promoting materials include hydroxyapatite ($Ca_{10}(PO_4)_6OH_2$), growth factors, bone morphogenic proteins, and mixtures thereof. The preferred bone ingrowth promoting material is hydroxyapatite.

As used herein to describe a material, the term "bioabsorbable" is used to define a material which will be completely assimilated by the body within a certain time period. The bioabsorbable material used in the coatings of the present invention should be non-toxic, biocompatible, and generally non-reactive with the bone ingrowth promoting material used in the coating. The products on absorption must likewise be biocompatible, non-toxic and non-reactive. Non-limiting examples of suitable bioabsorbable materials used in the coatings of the present invention include polylactic acid, polyglycolic acid, polylactic acid-polyglycolic acid copolymers, polydioxanone, polycaprolactone, polypeptides, polycarbonates, polyhydroxybutyrate, poly (alkylene oxalate), copolymers of vinyl acetates with unsaturated carboxylic acids (e.g. acrylic and methacrylic acids), water soluble or dispersible cellulose derivatives (e.g. methyl cellulose, hydroxymethylcellulose and carboxymethyl cellulose), ethylene oxide polymers, polyacrylamide, collagen, gelatin, poly(orthoester), polyamides of amino acids, polyvinyl alcohol, polyvinyl pyrrolidone, polyetheretherketone, tricalcium phosphate ($Ca_3(PO_4)_2$), and mixtures thereof. The preferred bioabsorbable material is tricalcium phosphate.

The first coating 24 and the second coating 25 for the prosthesis 20 of FIG. 2 may be formulated using any of the above bone ingrowth promoting materials and bioabsorbable materials. For example, (i) both the first coating 24 and the second coating 25 may comprise the same bone ingrowth promoting material and the same bioabsorbable material; (ii) the first coating 24 and the second coating 25 may comprise different bone ingrowth promoting materials and the same bioabsorbable material; (iii) the first coating 24 and the second coating 25 may comprise the same bone ingrowth promoting material and different bioabsorbable materials; or (iv) both the first coating 24 and the second coating 25 may comprise different bone ingrowth promoting materials and different bioabsorbable materials. Regardless of the particular formulation chosen for the first coating 24 and the second coating 25, it is a critical aspect of the invention that the first coating 24 and the second coating 25 provide for different bone affixation rates and/or final strengths of the prosthesis/implant bond. This will be explained in detail below.

Looking now at FIG. 3, there is shown another coated femoral prosthesis 30 in accordance with the present invention. The coated femoral prosthesis 30 includes a body 12 having a neck portion 13, a femoral head 14 and a collar 15, and a stem 16 as in the femoral prosthesis 10 of FIG. 1. The body and stem may be formed from the same materials as the femoral prosthesis 10 of FIG. 1. The stem 16 of the prosthesis 30 includes a proximal (or upper) portion 31, a middle portion 32 and a distal (or lower) portion 33. The outer surface of the proximal portion 31 of the stem 16 is coated with a first coating 35 (shown in cross-section) that includes a bone ingrowth promoting material and a bioabsorbable material as described above. The outer surface of the middle portion 32 of the stem 16 is coated with a second coating 36 (shown in cross-section) that includes a bone ingrowth promoting material and a bioabsorbable material as described above. The outer surface of the distal portion 33 of the stem 16 is coated with a third coating 37 (shown in cross-section) that includes a bone ingrowth promoting material and a bioabsorbable material as described above. The first coating 35 and the second coating 36 are arranged on the stem 16 of the prosthesis 30 such that the first coating 35 and the second coating 36 are in abutting relationship at an interface indicated at 44. The third coating 37 and the second coating 36 are arranged on the stem 16 of the prosthesis 30 such that the third coating 37 and the second coating 36 are in abutting relationship at an interface indicated at 45.

The first coating 35, the second coating 36 and the third coating 37 for the prosthesis 30 of FIG. 3 may be formulated using any of the above bone ingrowth promoting materials and bioabsorbable materials. In addition, the first coating 35, the second coating 36 and the third coating 37 may comprise the same or different bone ingrowth promoting materials and the same or different bioabsorbable materials. Regardless of the particular formulation chosen for the first coating 35, the second coating 36 and the third coating 37, it is a critical aspect of the invention that at least two of the first coating 35, the second coating 36 and the third coating 37 provide for different bone affixation rates and/or final strengths of the prosthesis/implant bond. This will be explained in detail below.

Figures 4, 5, 6:
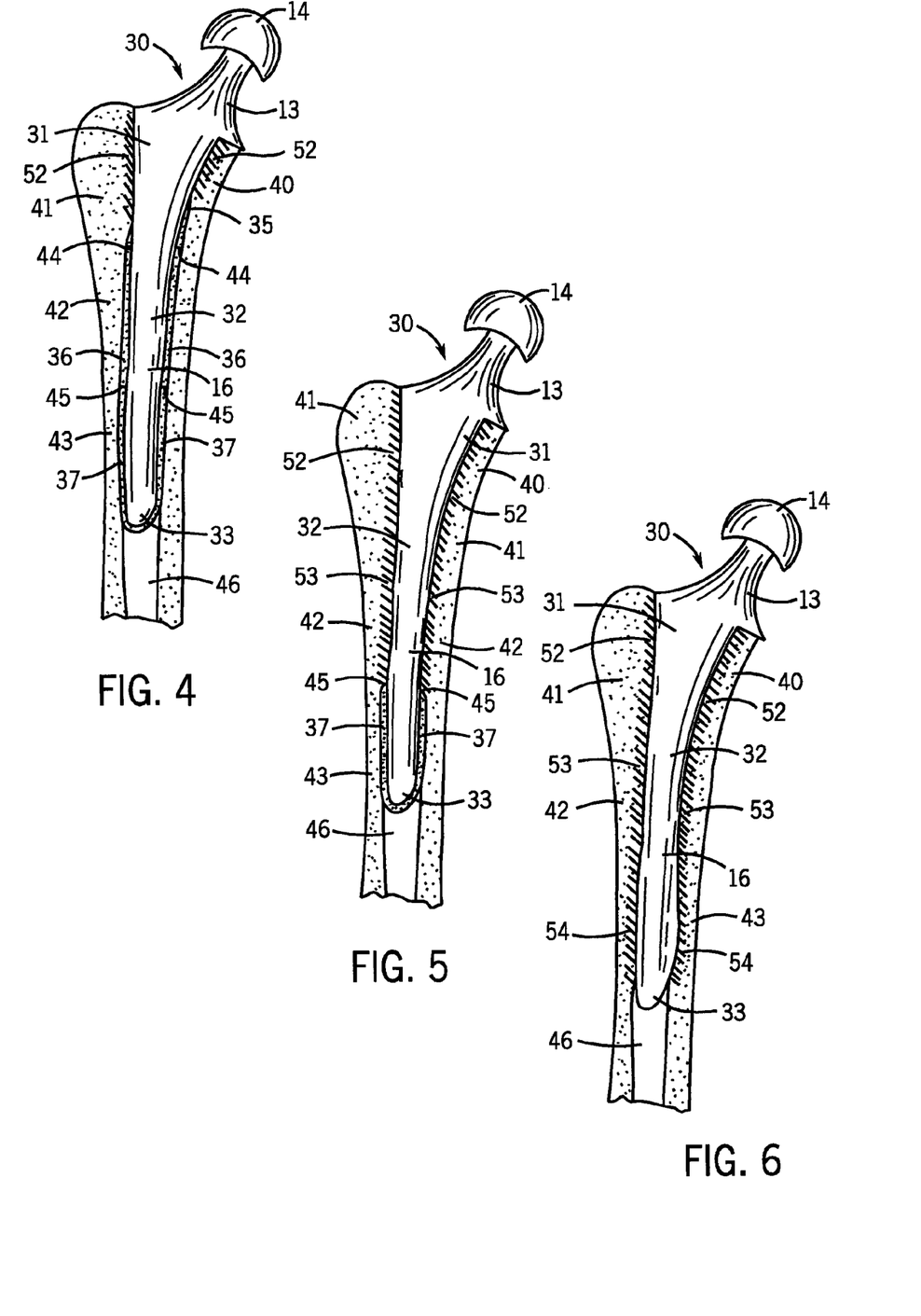
FIG. 4 is side view of the prosthesis of FIG. 3 as implanted in a femur after a first time period.
FIG. 5 is side view of the prosthesis of FIG. 3 as implanted in a femur after a second (longer) time period.
FIG. 6 is side view of the prosthesis of FIG. 3 as implanted in a femur after a third (even longer) time period.

Referring now to FIG. 4, there is shown the coated prosthesis 30 of FIG. 3 as implanted in a femur 40 (shown in cross-section) after a first time period. Before implantation of the prosthesis 30 in the femur 40, the prosthesis 30 includes a first coating 35 on the outer surface of the proximal portion 31 of the stem 16, a second coating 36 on the outer surface of the middle portion 32 of the stem 16, and a third coating 37 on the outer surface of the distal portion 33 of the stem 16 as shown in FIG. 3. In addition, before implantation of the prosthesis 30 in the femur 40, the first coating 35, the second coating 36 and the third coating 37 all comprise the same bone ingrowth promoting material (e.g., hydroxyapatite) and the same bioabsorbable material (e.g., tricalcium phosphate). However, a first ratio of the bone ingrowth promoting material to the bioabsorbable material in the first coating 35 is greater than a second ratio of the bone ingrowth promoting material to the bioabsorbable material in the second coating 36, and a third ratio of the bone ingrowth promoting material to the bioabsorbable material in the third coating 37 is less than the first ratio of the bone ingrowth promoting material to the bioabsorbable material in the first coating 35 and greater than the second ratio of the bone ingrowth promoting material to the bioabsorbable material in the second coating 36. It can be seen in FIG. 4 that the section of the femur 40 shown includes an upper section 41, a middle section 42 and a lower section 43. When the prosthesis 30 of FIG. 3 is implanted in the medullary canal 46 of the femur 40 (using known surgical methods), the first coating 35 of the prosthesis 30 is placed in contact with the upper section 41 of the femur 40, the second coating 36 of the prosthesis 30 is placed in contact with the middle section 42 of the femur 40, and the third coating 37 of the prosthesis 30 is placed in contact with the lower section 42 of the femur 40.

After implantation of the prosthesis 30 in the femur 40, bone affixation begins to occur along the outer surface of the stem 16 of the prosthesis 30. The rate of bone affixation is controlled by the composition of the first coating 35, the second coating 36 and the third coating 37. As detailed above, the first ratio of the bone ingrowth promoting material to the bioabsorbable material in the first coating 35 is greater than a second ratio of the bone ingrowth promoting material to the bioabsorbable material in the second coating 36, and the third ratio of the bone ingrowth promoting material to the bioabsorbable material in the third coating 37 is less than the second ratio of the bone ingrowth promoting material to the bioabsorbable material in the second coating 36. Therefore, while the first coating 35, the second coating 36 and the third coating 37 all comprise the same bone ingrowth promoting material (e.g., hydroxyapatite) and the same bioabsorbable material (e.g., tricalcium phosphate), the first coating 35 has the highest level of bone ingrowth promoting material and the lowest level of bioabsorbable material, the second coating 36 has an intermediate level of bone ingrowth promoting material and an intermediate level of bioabsorbable material, and the third coating 37 has the lowest level of bone ingrowth promoting material and the highest level of bioabsorbable material.

Until the bioabsorbable material is assimilated into the body, the bioabsorbable material acts as a shield to delay bone ingrowth onto and/or into the outer surface of the stem 16 of the prosthesis 30. In contrast, the bone ingrowth promoting material promotes ingrowth of bone onto and/or into the stem 16. By varying the ratio of bone ingrowth promoting material to bioabsorbable material, it is possible to vary the bone ingrowth rate onto and/or into the outer surface of the stem 16 of the prosthesis 30. For example, the first coating 35 has the highest level of bone ingrowth promoting material and the lowest level of bioabsorbable material, and therefore, will lead to the highest bone ingrowth rates onto and/or into the stem 16. The second coating 36 has an intermediate level of bone ingrowth promoting material and an intermediate level of bioabsorbable material, and therefore, will lead to an intermediate bone ingrowth rate onto and/or into the stem 16. The third coating 37 has the lowest level of bone ingrowth promoting material and the highest level of bioabsorbable material and therefore, will lead to the lowest bone ingrowth rates onto and/or into the stem 16.

The progress of bone ingrowth onto and/or into the stem 16 of the prosthesis 30 is shown sequentially in FIGS. 4–6. In FIG. 4, most of the bioabsorbable material in the first coating 35 has assimilated into the body, leaving behind a high level of bone ingrowth promoting material. As a result, bone affixation (indicated by lines 52) has occurred between the upper section 41 of the femur 40 and the proximal (or upper) portion 31 of the stem 16. At the same time, most of the bioabsorbable material remains in the second coating 36 (shown in cross-section) and the third coating 37 (shown in cross-section) thereby preventing bone ingrowth onto and/or into the middle portion 32 and the distal (or lower) portion 33 of the stem 16. In FIG. 5, most of the bioabsorbable material in the second coating 36 has assimilated into the body, leaving behind a high level of bone ingrowth promoting material. As a result, bone affixation (indicated by lines 53) has occurred between the middle section 42 of the femur 40 and the middle portion 32 of the stem 16. At the same time, most of the bioabsorbable material remains in the third coating 37 (shown in cross-section) thereby preventing bone ingrowth onto and/or into the distal (or lower) portion 33 of the stem 16. In FIG. 6, most of the bioabsorbable material in the third coating 37 has assimilated into the body, leaving behind a high level of bone ingrowth promoting material. As a result, bone affixation (indicated by lines 54) has occurred between the lower section 43 of the femur 40 and the distal (or lower) portion 33 of the stem 16.

It can be seen from a comparison of FIGS. 4–6 that by varying the ratio of bone ingrowth promoting material and bioabsorbable material in the first (upper) coating 35, the second (middle) coating 36 and the third (lower) coating 37, the bone affixation rates can be controlled from the top to the bottom of the stem 16. Therefore, early distal fixation of the femur 40 to the distal (or lower) portion 33 of the stem 16 can be avoided and rapid proximal fixation of the femur 40 to the proximal portion 31 of the stem 16 can be achieved. As a result, stress shielding is reduced in the prosthesis 30.

It can be appreciated that the stem of a prosthesis can have any number of coatings with varying ratios of bone ingrowth promoting material and bioabsorbable material. For example, the prosthesis 20 of FIG. 2 has two different coatings, which would lead to two bone affixation rates along the stem. The prosthesis 30 of FIG. 3, which is also depicted in FIGS. 4–6, provides three bone affixation rates along the stem. A prosthesis with four different coatings could provide four bone affixation rates along the stem, and so on.

Not only does a prosthesis according to the invention provide a solution to stress shielding problems, the prosthesis can be used to control the durability of different sections of the stem of the prosthesis. For example, by varying the ratio of bone ingrowth promoting material to bioabsorbable material in the three coatings for the proximal (or upper) portion 31, the middle portion 32 and the distal (or lower) portion 33 of the of the stem 16 of the prosthesis shown in FIGS. 3–6, it is possible to prepare a prosthesis implant where the proximal portion of the stem is most durable (e.g., it lasts years), the middle portion of the stem has an intermediate durability (e.g., it lasts~24 months), and the distal portion of the stem has the least durability (e.g., it lasts up to 12 months). This can be quite beneficial if the prosthesis has to be removed (as in revision surgery) because the distal portion of the stem will be easier to remove from the bone.

The bone ingrowth rates onto and/or into the stem 16 depends not only on the ratio of bone ingrowth promoting material to bioabsorbable material, but also on the particular bone ingrowth promoting material and bioabsorbable material selected. For example, the rate of degradation and assimilation of one bioabsorbable material into the body will be slower than that of another bioabsorbable material. Thus, the selection of the type of bioabsorbable material can be used to control the rate of assimilation. The assimilation rates of various bioabsorbable materials can be readily determined by those skilled in the art to enable selection of an appropriate bioabsorbable material for a specific application. Likewise, one bone ingrowth promoting material may promote faster bone ingrowth than that of another bone ingrowth promoting material. The rates of bone ingrowth for various bone ingrowth promoting materials can also be readily determined by those skilled in the art to enable selection of an appropriate bone ingrowth promoting material or mixture of bone ingrowth promoting materials for a specific application.

Therefore, in another embodiment of the invention, the rate of affixation along the length of the stem can be controlled not by varying ratios of one bone ingrowth promoting material and one bioabsorbable material in various coatings but by varying the bone ingrowth promoting material and the bioabsorbable material in each coating. For example, in the prosthesis 20 of FIG. 2, the first coating 24 may include a first bone ingrowth promoting material and a first bioabsorbable material, and the second coating 25 may include a second bone ingrowth promoting material and a second bioabsorbable material. It can be appreciated that the amount and the choice of bone ingrowth promoting materials and bioabsorbable materials is unlimited. However, it is a critical aspect of the invention that the first coating 24 and the second coating 25 provide for different bone affixation rates and/or final strengths of the prosthesis/implant bond. In this particular embodiment, the first coating 24 would have a combination of bone ingrowth promoting materials and bioabsorbable materials and the second coating 25 would have a combination of bone ingrowth promoting materials and bioabsorbable materials such that early distal fixation of the femur to the distal portion of the stem can be avoided and rapid proximal fixation of the femur to the proximal portion of the stem can be achieved.

While the control of bone affixation rates and final strengths at different locations on a prosthesis has been described above in relation to the stem of the femoral prosthesis component of an artificial hip joint, the above techniques can be used to affix any prosthesis to a bone. For instance, a first coating including a bone ingrowth promoting material as described above and a bioabsorbable material as described above can be applied to a first portion of the surface of a prosthesis, and a second coating including the bone ingrowth promoting material and the bioabsorbable material can be applied to a second portion of the surface of the prosthesis. The prosthesis is then located such that the first coating and the second coating are placed in contact with the bone. In this version of the invention, a first ratio of the bone ingrowth promoting material to the bioabsorbable material in the first coating is greater than a second ratio of the bone ingrowth promoting material to the bioabsorbable material in the second coating such that bone affixation rates and final strengths are different at the first portion and the second portion of the surface of the prosthesis. Alternatively, the first coating may include a first bone ingrowth promoting material and a first bioabsorbable material, and the second coating may include a second bone ingrowth promoting material and a second bioabsorbable material such that bone affixation rates and final strengths are different at the first portion and the second portion of the surface of the prosthesis.

Therefore, there has been provided an implantable bone prosthesis and associated surgical methods that solve the problems associated with stress shielding and that allow a surgeon to control bone affixation rates and final strengths at different locations on a prosthesis. While the implantation of the femoral prosthesis component of an artificial hip joint in the femoral medullary canal has been illustrated and described herein, one skilled in the art will appreciate that the present invention can be practiced by other than the described embodiments, which have been presented for purposes of illustration and not of limitation. For instance, the methods and prostheses according to the invention can be used in the repair of any bone or in connection with the implantation of prosthetic devices at or in any bone in the body. Accordingly, the scope of the appended claims should not be limited to the description of the embodiments contained herein.

What is claimed is:

1. A prosthesis for implanting into a bone having a cavity, the prosthesis comprising:
   a body;
   a stem fastened to the body at a proximal end and extending away from the body to form a distal end, the stem having an outer surface which is dimensioned to be inserted in the cavity of the bone;
   a first coating having a bone ingrowth promoting material that promotes ingrowth of bone onto the stem and having a bioabsorbable material that delays the ingrowth of bone onto the stem, the first coating being disposed on the proximal end of the outer surface of the stem; and
   a second coating having the bone ingrowth promoting material and having the bioabsorbable material, the second coating being disposed on the distal end of the outer surface of the stem,
   wherein a first ratio of the bone ingrowth promoting material to the bioabsorbable material in the first coating is greater than a second ratio of the bone ingrowth promoting material to the bioabsorbable material in the second coating.

2. The prosthesis of claim 1 wherein:
   the first coating and the second coating are disposed on the outer surface of the stem in abutting relationship.

3. The prosthesis of claim 1 wherein:
   the bone ingrowth promoting material is selected from hydroxyapatite, growth factors, bone morphogenic proteins, and mixtures thereof.

4. The prosthesis of claim 1 wherein:
   the bone ingrowth promoting material is hydroxyapatite.

5. The prosthesis of claim 1 wherein:
   the bioabsorbable material is selected from polylactic acid, polyglycolic acid, polylactic acid—polyglycolic acid copolymers, polydioxanone, polycaprolactone, polypeptides, polycarbonates, polyhydroxybutyrate, poly(alkylene oxalate), copolymers of vinyl acetates with unsaturated carboxylic acids, water soluble or dispersible cellulose derivatives, ethylene oxide polymers, polyacrylamide, collagen, gelatin, poly (orthoester), polyamides of amino acids, polyvinyl alcohol, polyvinyl pyrrolidone, polyetheretherketone, tricalcium phosphate, and mixtures thereof.

6. The prosthesis of claim 1 wherein:
   the bioabsorbable material is tricalcium phosphate.

7. The prosthesis of claim 1 wherein:
   the prosthesis is a femoral prosthesis.

8. The prosthesis of claim 1 wherein: the prosthesis is a tibial prosthesis.

9. The prosthesis of claim 1 wherein:
   the bone ingrowth promoting material is hydroxyapatite, and the bioabsorbable material is tricalcium phosphate.

10. The prosthesis of claim 1 further comprising:
    a third coating having the bone ingrowth promoting material and having the bioabsorbable material, the third coating being disposed on an intermediate portion of the outer surface of the stem between the proximal end of the outer surface of the stem and the distal end of the outer surface of the stem,
    wherein a third ratio of the bone ingrowth promoting material to the bioabsorbable material in the third coating is less than the first ratio of the bone ingrowth promoting material to the bioabsorbable material in the first coating, and wherein the third ratio of the bone ingrowth promoting material to the bioabsorbable material in the third coating is greater than the second ratio of the bone ingrowth promoting material to the bioabsorbable material in the second coating.

11. The prosthesis of claim 10 wherein
    the first coating and the third coating are disposed on the outer surface of the stem in abutting relationship, and
    the third coating and the second coating are disposed on the outer surface of the stem in abutting relationship.

12. The prosthesis of claim 10 wherein:
    the bone ingrowth promoting material is hydroxyapatite, and the bioabsorbable material is tricalcium phosphate.

13. A prosthesis for implanting into a bone having a cavity, the prosthesis comprising:
    a body;
    a stem fastened to the body at a proximal end and extending away from the body to form a distal end, the stem having an outer surface which is dimensioned to be inserted in the cavity of the bone;
    a first coating having a first bone ingrowth promoting material that promotes ingrowth of bone onto the stem and having a first bioabsorbable material that delays the ingrowth of bone onto the stem, the first coating being disposed on the proximal end of the outer surface of the stem; and
    a second coating having a second bone ingrowth promoting material and having a second bioabsorbable material, the second coating being disposed on the distal end of the outer surface of the stem,
    wherein the first coating and the second coating are formulated such that a first bone ingrowth rate onto the proximal end of the outer surface of the stem is greater than a second bone ingrowth rate onto the distal end of the outer surface of the stem, and
    wherein the first bioabsorbable material and the second bioabsorbable material are different.

14. The prosthesis of claim 13 wherein:
    the first coating and the second coating are disposed on the outer surface of the stem in abutting relationship.

15. The prosthesis of claim 13 wherein:
    the first bone ingrowth promoting material and the second bone ingrowth promoting material are selected from hydroxyapatite, growth factors, bone morphogenic proteins, and mixtures thereof.

16. The prosthesis of claim 13 wherein:
    the first bioabsorbable material and the second bloabsorbable material are selected from polylactic acid, polyglycolic acid, polylactic acid—polyglycolic acid copolymers, polydioxanone, polycaprolactone, polypeptides, polycarboriates, polyhydroxybutyrate, poly(alkylene oxalate), copolymers of vinyl acetates with unsaturated carboxylic acids, water soluble or dispersible cellulose derivatives, ethylene oxide polymers, polyacrylamide, collagen, gelatin, poly (orthoester), polyamides of amino acids, polyvinyl alcohol, polyvinyl pyrrolidone, polyetheretherketone, tricalcium phosphate, and mixtures thereof.

17. The prosthesis of claim 13 wherein:
    the prosthesis is a femoral prosthesis.

18. The prosthesis of claim 13 wherein:
    the prosthesis is a tibial prosthesis.

19. A prosthesis for implanting into a bone having a cavity, the prosthesis comprising:

a body;

a stem fastened to the body at a proximal end and extending away from the body to form a distal end, the stem having an outer surface which is dimensioned to be inserted in the cavity of the bone;

a first coating having a first bone ingrowth promoting material that promotes ingrowth of bone onto the stem and having a first bioabsorbable material that delays the ingrowth of bone onto the stem, the first coating being disposed on the proximal end of the outer surface of the stem; and a second coating having a second bone ingrowth promoting material and having a second bioabsorbable material, the second coating being disposed on the distal end of the outer surface of the stem, wherein the first coating and the second coating are formulated such that a first bone ingrowth rate onto the proximal end of the outer surface of the stem is greater than a second bone ingrowth rate onto the distal end of the outer surface of the stem, and wherein the first bone ingrowth promoting material and the second bone ingrowth promoting material are different.

20. A prosthesis for implanting into a bone having a cavity, the prosthesis comprising:

a body;

a stem fastened to the body at a proximal end and extending away from the body to form a distal end, the stem having an outer surface which is dimensioned to be inserted in the cavity of the bone:

a first coating having a first bone ingrowth promoting material that promotes ingrowth of bone onto the stem and having a first bioabsorbable material that delays the ingrowth of bone onto the stem, the first coating being disposed on the proximal end of the outer surface of the stem; and a second coating having a second bone ingrowth promoting material and having a second bioabsorbable material, the second coating being disposed on the distal end of the outer surface of the stem, wherein the first coating and the second coating are formulated such that a first bone ingrowth rate onto the proximal end of the outer surface of the stem is greater than a second bone ingrowth rate onto the distal end of the outer surface of the stem, wherein the first bioabsorbable material and the second bioabsorbable material are different, and wherein the first bone ingrowth promoting material and the second bone ingrowth promoting material are different.

\* \* \* \* \*

UNITED STATES PATENT AND TRADEMARK OFFICE
CERTIFICATE OF CORRECTION

PATENT NO. : 6,749,639 B2  Page 1 of 1
DATED : June 15, 2004
INVENTOR(S) : David G. Lewallen It is certified that error appears in the above-identified patent and that said Letters Patent is hereby corrected as shown below:

<u>Column 12,</u>
Line 49, "bloabsorbable" should read -- bioabsorbable --.
Line 53, "polycarboriates" should read -- polycarbonates --.

Signed and Sealed this

Twenty-first Day of September, 2004

JON W. DUDAS
*Director of the United States Patent and Trademark Office*